United States Patent
Pellaux et al.

(10) Patent No.: US 7,833,796 B2
(45) Date of Patent: Nov. 16, 2010

(54) METHOD FOR THE CONCENTRATION AND PURIFICATION OF BIOLOGICAL COMPOUNDS

(75) Inventors: Rene Pellaux, Zuerich (CH); Jens-Martin Heile, Ludwigsburg (DE); Andreas Josef Schenzle, Uhldingen-Muehlhofen (DE); Martin Held, Waiblingen (DE)

(73) Assignee: Preentec AG, Fribourg (CH)

( * ) Notice: Subject to any disclaimer, the term of this patent is extended or adjusted under 35 U.S.C. 154(b) by 1116 days.

(21) Appl. No.: 10/596,530

(22) PCT Filed: Dec. 15, 2004

(86) PCT No.: PCT/IB2004/004125

§ 371 (c)(1),
(2), (4) Date: Jun. 15, 2006

(87) PCT Pub. No.: WO2005/058453

PCT Pub. Date: Jun. 30, 2005

(65) Prior Publication Data

US 2007/0111194 A1 May 17, 2007

(30) Foreign Application Priority Data

Dec. 15, 2003 (CH) .................... 2135/03

(51) Int. Cl.
*G01N 33/48* (2006.01)

(52) U.S. Cl. .................... 436/86; 210/638; 210/660; 435/6; 436/178; 536/25.4; 536/25.41

(58) Field of Classification Search ............... 210/634, 210/635, 638, 645, 656, 660, 679, 681; 436/86, 436/89, 90, 161, 178, 190; 435/6, 270; 536/25.4, 536/25.41, 26.43; 560/241, 242; 502/400–402
See application file for complete search history.

(56) References Cited

U.S. PATENT DOCUMENTS

| | | | |
|---|---|---|---|
| 3,247,171 A | | 4/1966 | Walker |
| 4,902,559 A | * | 2/1990 | Eschwey et al. ............ 442/334 |
| 5,098,970 A | | 3/1992 | Hsieh |
| 5,856,192 A | * | 1/1999 | Bloch .......................... 436/18 |
| 6,855,434 B2 | * | 2/2005 | Romasn-Hess et al. .. 428/474.4 |
| 2002/0193030 A1 | * | 12/2002 | Yao et al. .................... 442/366 |
| 2003/0162853 A1 | | 8/2003 | Smiley |
| 2004/0029166 A1 | * | 2/2004 | Fan ................................. 435/6 |
| 2005/0131362 A1 | * | 6/2005 | Przepasniak et al. ........ 604/367 |
| 2005/0244882 A1 | * | 11/2005 | Gauch et al. .................. 435/6 |

FOREIGN PATENT DOCUMENTS

EP  530438  3/1993

OTHER PUBLICATIONS

Iritani, Iwata, and Murase, Separation Science and Technology 1993, 28 (10), 1819-36.

(Continued)

*Primary Examiner*—Joseph W Drodge
(74) *Attorney, Agent, or Firm*—Joyce von Natzmer; Pequignot + Myers LLC

(57) ABSTRACT

The invention concerns materials and methods used for the concentration, desalination, purification or stabilization of biological compounds, in particular biological macromolecules and supramolecular structures, by means of superabsorbent polymers or superabsorptive composite materials.

28 Claims, 1 Drawing Sheet

OTHER PUBLICATIONS

Prazeres, Journal of Biotechnology 1995, 39 (2), 157-64.
Chacon, Hsieh, Hurth, and Krochta, Polymer 2000, 41 (23), 8257-8262.
Iritani, Mukai, and Ueki, Funtai Kogaku Kaishi 2001, 38 (8), 555-561. (Abstract Only).
Iritani, Mukai, Ueki, and Katagiri, Funtai Kagaku Kaishi 2003, 40 (1), 4-10. (Abstract Only).
Badiger, et al., Chemical Engineering Science 1992, 47 (1), 3-9.
Vasheghani-Farahani, et al., Chemical Engineering Science 1992, 47 (1), 31-40.
Davies, et al., Environmental Technology 2004, vol. 25, 89-100.

* cited by examiner

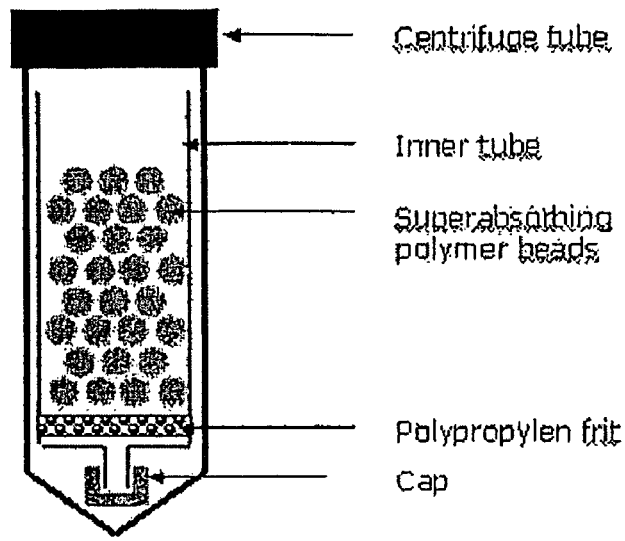
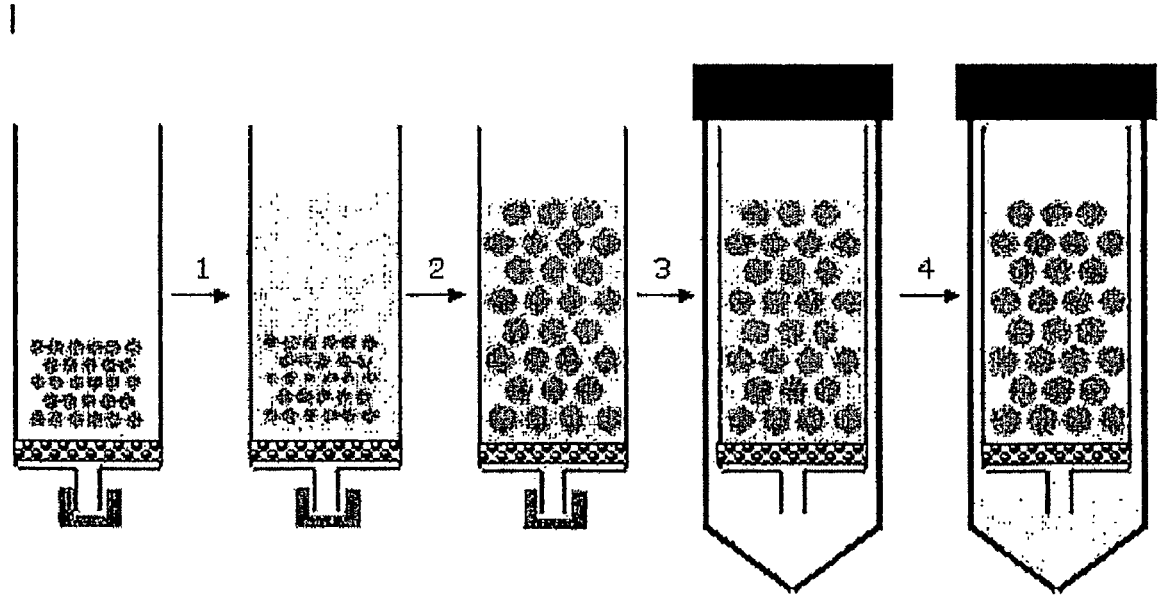

METHOD FOR THE CONCENTRATION AND PURIFICATION OF BIOLOGICAL COMPOUNDS

This is the U.S. national stage of International application PCT/IB2004/004125, filed Dec. 15, 2004 designating the United States.

FIELD OF INVENTION

The present invention relates to materials and methods for the concentration, desalination, purification and/or stabilization of biological compounds, in particular biological macromolecules and supramolecular structures, by means of superabsorbent polymers or superabsorptive composite materials.

BACKGROUND

Superabsorptive polymers are mainly used as water absorbing agents in diapers or as humidity control agents in medical devices such as wound dressings. The materials usually contain of acrylic acid and acrylamide or of derivative of these monomers and a bisacrylic crosslinker. Information on the synthesis and absorption characteristics of such specific superabsorbing polymers have been previously described (Buchholz 1998).

Some superabsorbing polymers can also be used for the purpose of size-exclusive concentration of polypeptides (Chacon 2000, Iritani 1993, 2001, 2003, Prazeres 1995). However, as the superabsorbing polymers were not designed for this purpose, the corresponding processes have had limited success, especially with regard to concentration, protein yields and handling.

Sorptive composite materials have been described in WO 03/037505 (PCT/EP02/12050). These materials are composites of crosslinked acrylic polymers and one or more sorbent materials, where the sorbent is enveloped by the acrylic polymer and binds the sorbate, which is later eluted. The sorbent may also be used to separate impurities and undesired side-product from cells in cell culture or other liquid phases in nature, such as seas, rivers, springs, lakes, ponds, communal or industrial waste or process-water streams. The polymer material can be designed in such a fashion that the polyacrylamide/polyacrylic composite materials mediate size-exclusive properties during sorption, allowing bigger molecules to have a lower or infinite penetration rate through the polyacrylic hydrogels than smaller molecules. The polymeric materials are typically in the form of a hydrogel containing 20 to 95% water to allow diffusion of the sorbate, while the sorbent remains entrapped.

There remains a need for materials and methods for concentrating, desalting, purifying and/or stabilizing biological compounds and this invention meets those needs.

RELEVANT LITERATURE

Bucholz 1998: Bucholz F. L.; Graham A. T.; Eds., Modern superabsorbent polymer technology", Wiley-VCH, New York 1998.
Chacon 2000: Chacon D.; Hsieh, Y. -L.; Kurth M. J.; Krochta J. M.; Swelling and protein absorption/desorption of thermo-sensitive lactitol-based polyether polyol hydrogels; Polymer 2000, 41(23), 8257-8262.
Iritani 1993: Iritani, E.; Iwata M.; Murase T.; Concentration of proteinaceous solutions with superabsorbent hydrogels; Separation Science and Technology 1993, 28(10), 1819-36.
Iritani 2001: Iritani E.; Mukai Y.; Ueki, C.; Concentration and desalination of protein solutions with superabsorbent hydrogels; Funtai Kogaku Kaishi 2001, 38(8), 555-561.
Iritani 2003: Iritani, E.; Mukai, Y.; Ueki, C.; Katagiri, N.; Simultaneous operation of fractionation and concentration of binary protein mixture with particles of superabsorbent hydrogel; Funtai Kagaku Kaishi 2003, 40(1),-4-10.
Prazeres 1995: Prazeres, D. M.; Concentration of BSA using a superabsorbent polymer: process evaluation; Journal of Biotechnology 1995, 39(2), 157-64.

BRIEF DESCRIPTION OF THE DRAWINGS

FIG. 1: Example of a device used for the concentration of samples.

The device has an outer centrifuge tube, an inner tube that contains the superabsorbing polymer beads and is locked at the lower end with a cap. Concentration of a sample can be performed by the following steps: 1) addition of 10 ml sample to the inner tube. 2) incubation of sample in the inner tube for 20 minutes. 3) removal of the lower cap and positioning of the inner tube into the a centrifuge tube. 4) centrifugation of the device for 5 minutes at 3000 rpm, whereby the sample is collected in the centrifuge tube.

SUMMARY OF THE INVENTION

The present invention provides methods of concentrating and purifying a target entity in a liquid sample, by contacting the sample with a superabsorbent polymer or a superabsorptive composite material to allow at least a portion of the sample to be absorbed by the polymer or composite material. The target entity may be dissolved or suspended in the sample, which may contain additional dissolved compounds or materials, such as salts.

In one aspect, the superabsorbent polymer or the superabsorbing composite material absorbs the solvent from the sample, thereby reducing the volume of the sample (i.e., effectively concentrating the sample). The superabsorbent polymer or the superabsorbing composite material may absorb dissolved compounds, in particular salts, in the sample, thereby allowing desalination of a sample.

The method is preferably carried out with a superabsorbent polymer, in the absence of a sorbent dispersed therein.

The solvent is typically a hydrophilic solvent, preferably water or a mixture of water and a water miscible solvent.

In another aspect of the invention, the method further incorporates the step of separating the target entity from the swollen superabsorbing polymers or superabsorbing composite materials.

The target entity can be a peptide or polypeptide, such as an enzyme, an antibody or antibody fragment, an interferon, a blood clotting factor, erythropoietin, insulin, a hormone or a cytokine. Alternatively the target entity can be an oligosaccharide, a polysaccharide or a polyketide. The target entity can be a nucleic acid, such as a single-stranded or double-stranded DNA or RNA, or combination thereof, preferably genomic, viral or plasmid DNA, cDNAs, PCR products or viral RNA. Alternatively, the target entity can be a viral particle, preferably an adenovirus, adeno-associated virus, retrovirus, lentivirus, poxvirus or herpes virus.

Also provided by the invention are superabsorbing polymers comprising polymerized vinylic monomers and anionic, cationic and/or zwitterionic monomers. Preferably the vinylic monomers are acrylic monomers, acrylic acid or methacrylic acid derivatives, or mixtures thereof. Preferably, the acrylic acid and/or methacrylic acid derivatives are amides and/or esters thereof. The superabsorbing polymer preferably contains polymerized ionized or ionizable acrylic monomers, preferably present in concentrations of 0.1-100% of the total monomers. Preferred superabsorbing polymers contain polymerized acrylate, 3-(methacryloylamino)propyl trimethylammonium chloride and/or [3-(methacryloylamino)propyl]dimethyl(3-sulfopropyl)ammonium hydroxide.

The superabsorbing polymer is typically crosslinked, preferably with a crosslinking degree of 0.0001-10%, further preferred with a crosslinking degree of 0.01-1%. Optionally, the superabsorbing polymer contains a sorbent dispersed in the polymer.

The properties of the superabsorbing polymers lead to swelling of the polymer upon contact with water or an aqueous solution.

The superabsorbing polymers of the invention are provided as powders, beads, preferably with a diameter in the range of 0.001-10 mm, more preferably with a diameter in the range of 0.1-4 mm and surface coatings.

Also provided are devices comprising superabsorbing polymers, which may have a container, such as a sample tube, a centrifuge tube, a pipette tip, a column, a syringe or a microtiter plate with the superabsorbing polymer filled into, bound to, or polymerized onto the container.

Also provided are processes for making a superabsorptive polymer, comprising hydrolysis of cross-linked polyacrylamide, for example by treating the cross-linked polyacrylamide with alkali.

Alternatively, or in addition, the process for making a superabsorptive polymer comprises polymerizing ionized or ionizable acrylic monomers in the presence of a cross-linking agent.

DESCRIPTION OF SPECIFIC EMBODIMENTS

The present invention provides novel methods and superabsorbing polymers or superabsorbent composite materials designed for concentrating a broad variety of macromolecules or supermolecular structures in solution with high yield and efficiency. By "superabsorbing" or "superabsorbent" as used herein, it is meant that the polymers or materials have the characteristics of sorbing water or hydrophilic liquids, as well as low molecular weight materials, in particular salts, in copious amounts. It is not only possible to concentrate the desired target entities with such superabsorbing polymers or superabsorbent composite materials but the entities can also be purified by simultaneous depletion of low molecular weight impurities from the sample.

Thus in one aspect of the invention, a method is provided that involves contacting a sample containing the target structure of interest, with a superabsorbent polymer or superabsorptive composite material to absorb at least a portion of the sample by the polymer or composite material. In this context, the superabsorbing polymers and superabsorptive composite materials are used for concentration, desalination, purification or stabilization of samples, preferably samples containing biological compounds. For a more complete understanding of the invention, one should consider certain global issues relating to (1) the important features of the superabsorbent polymer or superabsorptive composite material; (2) the nature of the sample; and (3) the nature of the concentration and/or purification.

According to the present invention, superabsorbing polymers or the superabsorbing component of superabsorbing composite materials are natural, semi-synthetic or synthetic, cross-linked, hydrophilic polymers. The superabsorbing polymer used in the methods of the invention is a co-polymer of vinylic monomers and anionic, cationic and/or zwitterionic monomers. Preferred monomers are vinylic monomers, such as acrylic monomers, preferably monomers of derivatives of acrylic acid or methacrylic acid, even more preferably amide or ester derivatives of acrylic acid and methacrylic acid, or mixtures thereof. Indeed, to provide the superabsorbant properties to the polymer, the polymer contains ionized or ionizable monomers, preferably acrylic monomers, preferably in concentrations of 0.1-100% mole/mole of the total monomer concentration used in synthesizing the polymer. Preferred ionized or ionizable monomers include acrylic acid and its salts, methacrylic acid and its salts, [3-(methacryloylamino)propyl]trimethylammonium chloride, and [3-(metha-cryloylamino)propyl]dimethyl(3-sulfopropyl)ammonium hydroxide). Further handling of the polymer during synthesis may be needed to provide superabsorbant properties, as is described in more detail below. The superabsorbant polymer produced in this way has ionized or ionizable groups and typically undergoes swelling upon contact with water or an aqueous solution, thereby absorbing large amounts of water or aqueous solute.

Preferred cross-linking agents are bifunctional acrylic monomers, preferably N,N'-methylenebisacrylamide and N,N'-ethylenebisacrylamide. Preferably the degree of crosslinking within the polymer is 0.0001-10%, more preferably 0.01-1%.

In addition to above mentioned properties, superabsorptive composite materials contain at least one additional component, such as a sorbent, magnetic materials, density-influencing agents or other materials facilitating separation of the composite material from the sample. A magnetic material is preferably a finely powdered compound that is attracted by a permanent magnet or an electromagnet. Magnetic compounds are preferably chosen from the group of compounds comprising metals, metal alloys and metal oxides. Further preferred metal oxides are ferrites, further preferred ferrite is magnetite, further preferred is magnetite with a particle size smaller than 5 microns. The superabsorbing composite materials comprising one or more additional components can be produced by suspending finely dispersed particles (e.g., sorbent particles) in the precursor solution prior to or during synthesis. However, the presence of a sorbent is not needed for the superabsorptive properties of the polymers in the present invention and need only optionally be included as a composite material. As some sorbents interfere with biologically active molecules, preferred superabsorptive polymers do not include a sorbent dispersed in the polymer.

Preferred sorbents are inorganic solids such as elementary metals, non metals and their compounds. Preferred compounds are oxides, hydroxides, carbonates, silicates, phosphates, sulfates and halogenides. Preferred oxides are the oxides of aluminum, magnesium, silicon, titanium and zirconium. Further preferred are porous aluminum oxides and silica gels as they are used in chromatography and solid phase extraction. Examples of such silica gels include functionalized silica gels as octadecyl-, octyl-, cyclohexyl-, phenyl-, ethyl-, cyanopropyl- and propanediolpropanediol-functionalized silica gels. Other preferred silica include celite®, talcum, magnesia silicates such as florisil®, zeolites and molecular sieves, clays as kaolin, montmorillonites, organically modified montmorillonites, bentonites, and fullers' earths. Other preferred inorganic solids are hydroxyapatite, graphite and activated charcoals.

Further preferred sorbents include organic solids such as natural, semisynthetic or synthetic polymers. Preferred polymers include poly(hydroxyalkanoates), polylactate, polybutyrate and polysaccharides. Further preferred polysaccharides are cellulose and derivatives of cellulose as well as agarose and derivatives of agarose. Preferred synthetic polymers are crosslinked polystyrenes as well as chemically functionalized polystyrenes (see Example 12) such as commercially available strong or weak cation- or anion exchangers. Other preferred synthetic polymers include chelating sorbents, affinity sorbents and molecular imprinted polymers.

A superabsorptive polymer according to the present invention is preferably prepared by free radical polymerization from a mixture comprising acrylic monomer, cross-linking agent, and water. The acrylic monomer can be an ionized or ionizable acrylic monomer, such as acrylic acid and its salts, methacrylic acid and its salts, [3-(methacryloylamino)propyl]trimethylammonium chloride, and [3-(metha-cryloylamino)propyl]dimethyl(3-sulfopropyl)ammonium hydroxide) (see Examples 7 and 10), requiring no further treatment after polymerization to exhibit superabsorbant properties. Optional additives such as magnetic compounds, density-influencing agents or sorbents may be added as described above. Further a commonly used polymerization initiator and accelerator such as potassium persulfate and N, N,N', N' tetramethylethylenediamine may be added. Different methods for initiating and accelerating the polymerization such as the application of radiation, preferably ultraviolet light or X-ray, or heat may be used.

Thus, in one aspect, the invention provides a process form making a superabsorptive polymer, said process comprising polymerizing ionized or ionizable acrylic monomers in the presence of a cross-linking agent.

In a further aspect of the invention, when an acrylic monomer is used to synthesize a superabsorbing polymer, the cross-linked polymer, e.g., polyacrylamide obtained by this process is subjected to hydrolysis to produce a polymer with superabsorbant properties. Hydrolysis is easily achieved by alkali treatment of the polymer, in particular polyacrylamide, for example by boiling the polymer in the presence of potassium hydroxide as is exemplified below in Example 3. Thus also provided by the invention is a process for making a superabsorptive polymer, comprising hydrolysis of cross-linked polyacrylamide, in particular by treating the cross-linked polyacrylamide with alkali.

The superabsorbant polymers or superabsorbant composite materials can be produced as powders, particles or surface coatings. In preferred embodiment, they are produced as spherical particles (beads), more preferably spherical particles of diameter in the range of 0.001-10 mm, even more preferably of diameter in the range of 0.1-4 mm. It is an important advantage of such spherical shaped particles that mechanical stress and attrition due to contact is greatly reduced due to reduced friction and shearing. Therefore, the superabsorbing polymer or superabsorbent composite materials disclosed herein are very suitable for use in biotechnological processes and experiments wherein agitation and stirring is regularly required. In order to synthesize spherical particles of superabsorbing polymer or superabsorbent composite materials a mixture of appropriate monomers, cross-linking agent, and water is prepared.

Addition of polymerization accelerator may be desired to promote the reaction but is not a requirement. Preferably, the mixture is prepared by combining aqueous solutions of appropriate monomers and a cross-linking agent, followed by the addition of the polymerization accelerator. By way of example, this mixture may be prepared by mixing 12 ml 4 wt % aqueous sodium alginate, 5 ml water, 8 ml 40 wt % aqueous acrylamide and 4 ml 2 wt % aqueous N, N'-methylenebisacrylamide, and 1 ml 10 wt % aqueous N, N,N', N'-tetramethylethylenediamine (see Example 1). As is apparent to one of ordinary skill in the art, variations in the composition of the mixture and ratios of the various components are possible (see, for example WO03/037505 page 13) dependent on the desired properties of the resulting polymer and synthetic procedure employed for their production.

Droplets of the mixture are dripped into a hardening solution, which comprises an aqueous phase, preferably water, and an ionotropic gelling inducer essentially as described in WO 03/037505 (page 14, see also Example 1). Droplets of the mixture can be prepared by various techniques. If the required size of droplets is in the range of 1 mm to 4 mm they may be prepared by pumping the mixture through an orifice of appropriate size. If smaller droplets are required, standard techniques for droplet-formation such as laminar jet break-up technology and commercially available equipment may be used. The hardening solution preferably contains a polymerization inducer. Upon submersion of the droplets in the hardening solution beads are formed due to fast reaction of the ionotropic gelling agent with the ionotropic gelation inducer. The beads comprising monomer and cross-linking agent are then allowed to undergo free radical polymerization to form a cross-linked acrylic polymer. During this process the hardening solution can be stirred to keep the beads in motion and avoid their agglomeration. When the polymerization is completed the beads are separated from the hardening solution by sieving, for instance, and washed with water.

An ionotropic gel which may be present in the polymer, as in Example 1, and may be resolved or destabilized and subsequently partially or totally removed by treatment with a chelating agent such as water-soluble salts of phosphate, citrate or ethylene diamine tetraacetate (EDTA). Preferably, removal of the calcium alginate gel is done by repeated treatment of the particles with an aqueous solution of sodium citrate or sodium phosphate, preferably in the concentration range of 0.01-0.2 M, more preferably in a concentration of 0.1 M. The polymer may optionally be subjected to alkali hydrolysis as described above, depending on the monomer composition and the requirement to form a superabsorbent material. The resulting particles of the superabsorbant polymers or superabsorbant composite materials may be dehydrated at temperatures in the range from 0-100 C. The dehydration may be effected at normal pressure or under reduced pressure.

The methods disclosed herein comprise the concentration, desalination, purification and stabilization of a sample. Samples can be of any type but of particular interest are samples from the following origins: human, animal or plant tissues, cell cultures, tissue cultures, bone marrow, human or animal body fluids such as blood, serum, plasma, urine, sperm, cerebro-spinal fluids, sputum, swabs, human or animal faeces, plants, plant-parts and extracts, prokaryotic or eukaryotic microorganisms such as bacteria, fungii and yeasts, viruses, soil samples, mud, waste water, drinking water or food. The sample may originate from a healthy donor, or from a diseased or abnormal donor, thereby potentially allowing diagnostic analysis from a sample.

In some embodiments, the biological material may need pre-treatment, such as, requiring the preparation of a cell, chloroplast, nuclear or organelle extract. Methods for the preparation of such extracts are well known in the art (for example, see Scopes, 1987, Protein Purification: Principles and Practice, Second Edition, Springer-Verlag, N.Y.) and may comprise simply cell lysis using mechanical means, detergents or salts. Cellular debris may optionally be removed, for example by centrifugation, prior to contact of the sample with the superabsorbent polymers or the superabsorbing composite materials.

According the invention, preferred target entities within the sample are molecules or supramolecular structures in samples that have to be concentrated, desalinated, purified or stabilized. Preferred target entities are natural, semisynthetic or synthetic macromolecules, in particular biological polymers or oligomers, in particular polymeric or oligomeric saccharides, amino acids or nucleic acids, or other natural products such as polyketides, antibiotics and the like. Preferred polymeric or oligomeric amino acids can be a peptide, a polypeptide, a protein, an enzyme, an antibody or antibody fragment, an interferon, a blood-clotting factor, erythropoietin, insulin, interferon, a hormone or a cytokine. Preferred oligonucleotides or polynucleotides are single-stranded or double-stranded DNA or RNA molecules (including hairpin structures and partially double-stranded molecules), preferably genomic, viral, or plasmid DNA, cDNAs, PCR products or viral RNA. The biological polymers may be naturally occurring or may be synthesized by recombinant, chemical or other means. Thus, the biological polymers may contain non-naturally occurring amino acids, nucleotides and sugars. Further target entities are supramolecular structures, in particular biological supramolecular structures such as a viral particle, more preferably adenovirus, adeno-associated virus, retrovirus, lentivirus, poxvirus, HIV or herpes virus. Further preferred are viruses that are used for gene transfer in gene therapy.

According to the invention, samples are liquids or liquefied mixtures of a target entity and a liquid, whereby the target entity is preferably dissolved or suspended in the mixture. Preferably the liquid is a hydrophilic solvent, such as water or an aqueous solute, or a mixture of water and a water-miscible solvent, such as acetonitrile. In addition to the target entity and the solvent, the sample may contain one or more additional components, such as salts or impurities, which typically will also be dissolved in the mixture.

The present invention provides methods of concentrating and purifying a target entity, such as a biological compound, in a liquid sample, by contacting the sample with a superabsorbent polymer or the superabsorptive composite material. Upon contact of the superabsorbent polymer or the superabsorptive composite material and the sample within an appropriate contact time, one or more of the components in the sample are absorbed by the superabsorbing polymer or the superabsorbing composite material.

If upon contact of the superabsorbent polymer or the superabsorptive composite material with the sample for an appropriate contact time, the solvent is more efficiently sorbed than the target structure, the target structure is concentrated. If complete absorption of the solvent in a sample is achieved, the method can be used for sample-drying and stabilization of the target entity, preferably from degradation as is exemplified in Examples 8 and 9 below. If upon contact of the superabsorbent polymer or the superabsorptive composite material with the sample for an appropriate contact time, salts or salts and solvent are more efficiently sorbed than the target structure, the target structure is desalinated or desalinated and concentrated, respectively. If upon contact of the superabsorbent polymer or the superabsorptive composite material with the sample for an appropriate contact time, the impurities or the impurities and the solvent are more efficiently sorbed than the target structure, the target structure is purified or purified and concentrated, respectively. The appropriate contact time will be dependent on the amount, shape and composition of the superabsorbent polymer or the superabsorbent composite material, on the volume of the sample, on the temperature of the sample and on the desired degree of concentration, desalination or purification, and is easily ascertainable by the practitioner. Preferred contact times are in the range of 1 second to 24 hours, more preferred in the range of 5 seconds to 1 hour.

In a further aspect of the invention, the methods further comprise the step of separating the target entity from the superabsorbing polymer or the superabsorbing composite material after concentrating, desalting, purifying or and/or stabilizing the target entity. Preferred separation steps include without limitation decantation, filtration, pipetting and centrifugation or the use of methods dependent on magnetism.

The methods of the invention can be facilitated using a device designed for contacting the superabsorbing polymer or the superabsorbing composite material with the sample and optionally separating the target entity from the superabsorbing polymer or the superabsorbing composite after the contact. The device can be made up of a wide variety of components according to the present invention, depending upon the intended user of the device and the particular needs of the user. An illustrative device for performing the methods of the invention is provided below. Such a device can be prepared from readily available materials and reagents and can be easily varied as is apparent to one of ordinary skill in the art. The device preferably has a container, such as a sample tube, a centrifuge tube, a pipette tip, a column, a syringe and/or a micro-titer plate. The superabsorbing polymer or the superabsorbing composite material preferably is filled into, bound to, or polymerized onto the container. Contact of the sample and the superabsorbing polymer or the superabsorbing composite material is made by either filling the sample into the container or dipping the container into the sample. After an appropriate contact time between the sample and the superabsorbing polymer or the superabsorbing composite material of the container, the target structure is separated from the superabsorbing polymer or the superabsorbing composite material by at least one separation step. In principle, any method of contacting the sample and the container or separating the target structure and the container can be used such as is evident to those skilled in the art.

A preferred device of the invention for the concentration of samples is illustrated in FIG. 1. The device has an outer container, such as a centrifuge tube, with at least one aperture to receive an inner container, such as a tube. The inner container therefore fits into the outer container and further has an aperture at each end. The inner container contains the superabsorbing polymer or superabsorbing composite material, preferably in bead form, optionally over a frit or other means to restrict loss of the superabsorbing polymer or superabsorbing composite material. The inner container is also blocked at one end with a removable cap, plug or other means for restricting the flow of sample out of the inner container until desired. Concentration of a sample using such a device can be performed by the following steps: 1) adding a sample (e.g., 10 ml) to the inner container, 2) incubating the sample in the inner container for an appropriate length of time to achieve the desired result (e.g. 20 minutes), 3) removing the removable cap, plug or other blocking means and positioning the inner container into the outer container and 4) centrifuging the device under appropriate conditions to allow collection of the sample in the outer container (e.g., 5 minutes at 3000 rpm).

As is apparent to one of ordinary skill in the art, such a device can easily be adapted to suit the particular needs of the practitioner. For example, the device may include only the inner container described above and the treated sample may be recovered by gravity, pressure or other means, rather than by centrifugation. Similarly, containers comprising a superabsorbing polymer or superabsorbing composite material with only one aperture for applying the sample are also envisioned, where the treated sample can be simply decanted or aspirated. Thus, the superabsorbing polymer or superabsorbing composite materials can be filled into, bound to, or polymerized onto a container, such as a sample tube, a centrifuge tube, a pipette tip, a column, a syringe or a microtiter plate to provide a device of the invention.

The following examples describe specific aspects of the invention to illustrate the invention and provide a description of the present superabsorbent polymers and methods for those of skill in the art. The examples should not be construed as limiting the invention, as the examples merely provide specific methodology useful in understanding and practice of the invention.

EXAMPLES

Example 1

Procedure for the Synthesis of Spherical Particles of poly(acrylamide-co-N,N'-methylenebisacrylamide)

Aqueous sodium alginate (12 ml; 4% w/v, low viscosity, Sigma), water (5 ml), aqueous acrylamide (8 ml, 40% w/v, purum, Fluka), aqueous N,N'-methylene-bisacrylamide (4 ml, 2% w/v), and N,N,N',N'-tetramethylethylendiamine (0.1 ml in 1 ml water) were mixed to give a precursor solution. The precursor solution is then filled into a syringe (1.4 mm diam. syringe needle) and dripped with the aid of a syringe pump (10 ml per min) into a beaker filled with a stirred solution of ammoniumperoxodisulfate (60° C., 80 ml, 1% w/v, containing 0.1 M calcium chloride, 30 min incubation) upon which spherical beads are formed. The beads were separated from the hardening solution by sieving, washed with water (5 times 100 ml), matured in an aqueous solution of sodium-citrate (100 ml, 0.1 M, 6 h, RT) and washed (5 times 100 ml water). Citrate treatment and washing steps were repeated twice. After synthesis the resulting poly(acrylamide-co-N,N'-methylenebisacrylamide) beads can be stored in water.

Alternatively, droplet formation and bead synthesis can be done by aid of an encapsulator system (Nisco Engineering, nozzle size 0.08 mm to 0.6 mm) which allows for smaller bead size (0.1-1.2 mm).

Example 2

Procedure for the Polymerization of Poly(Acrylamide-co-N,N'-methylenebisacrylamide) on the Inner Surface of Plastic Tubes Aqueous solutions of acrylamide (8 ml, 40% w/w, purum, Fluka) and N,N'-methylenebisacrylamide (4 ml, 2% w/v) were mixed and aqueous solutions of ammonium peroxodisulfate (0.12 ml, 2% w/v, MicroSelect, Fluka) und sodium pyrosulfate (0.12 ml, 2% w/v, purum, Fluka) were added. The mixture was immediately transferred to Eppendorf tubes (0.5 ml per tube), allowed to polymerize in a thermomixer (80°, 2 h) and dried (950, 12 h).

Example 3

Procedure for Synthesis of Spherical Particles of poly(acrylamide-co-potassium acrylate-co-N,N'-methylenebisacrylamide) by Basic Hydrolysis of poly(acrylamide-co-N,N'-methylenebisacrylamide)

Poly(acrylamide-co-N,N'-methylenebisacrylamide) beads (100 g, prepared according to the method of Example 1) were boiled in aqueous potassium hydroxide (500 ml, 5% w/v, 5 h) and recovered by sieving, incubated in water (three times, 5 L, 2 h) and dried (room temperature or elevated temperature e.g. in an oven at 80°). The weight of the poly(acrylamide-co-potassium acrylate-co-N,N'-methylenebisacrylamide) dried beads was 7.8±0.5 mg and 203±10 mg after contacting with water (distilled water, 10 ml per bead, RT, 3 h).

Example 4

Procedure for the Concentration of DNA by Spherical Particles of poly(acrylamide-co-potassium acrylate-co-N,N'-methylenebisacrylamide)

In their dry state, the superabsorbing polymer particles of Example 3 have a diameter of about 2 mm. The swelling properties of the particles are dependent on ion concentration and pH, which can be chosen by the user to obtain the desired effect. In 40 mM NaCl, the particles have a diameter of about 6.5-7 mm and absorb 140-175 µl of liquid each.

The DNA concentration capacity of the beads were assessed on a 1 ml-scale by incubating plasmid DNA (20 µg/ml, 4.5 kb) with 0, 3, 4 or 5 dried spherical beads of superabsorbing polymers produced according to example 3. The remaining liquid was recovered after 20 min by pipetting and the DNA concentration was determined spectrophotometrically. Absorption values of control experiments (40 mM NaCl alone; 0, 3, 4, or 5 beads/ml) were subtracted from experimental values (DNA, 40 mM NaCl; 0, 3, 4, or 5 beads/ml). The results are presented in Table 1 below and demonstrate that the DNA concentration in the recovered liquid is proportional to the reduction in volume.

TABLE 1

| Beads/ml | Relative DNA concentration (OD260) | Volume reduction |
| --- | --- | --- |
| 0 | 1 | 1 |
| 3 | 1.67 | 1.75 |
| 4 | 2.28 | 2.21 |
| 5 | 3.33 | 3.73 |

The beads prepared according to Example 3 were also tested for their capability of concentrating nucleic acid of various other types. Genomic DNA (20 µg), plasmid DNA (20 µg), PCR product (20 µg) and an oligonucleotide (14 µg) were contacted with 0 or 4 spherical beads of superabsorbing polymer. The remaining liquid was recovered after 20 min of incubation by pipetting, the DNA concentration determined spectrophotometrically and equal volumes of the recovered liquid were analyzed by electrophoresis (1% agarose gel; 2% for the oligonucleotide). The gel was stained with ethidium bromide and DNA-ethidiumbromide adducts were visualized under UV light. Samples were compared to a λ Hind III size standard. The results are presented in Table 2.

TABLE 2

|  | No beads | 4 beads | Factor | Recovery |
|---|---|---|---|---|
| A. Genomic DNA from blood (approx. 30 kb) | | | | |
| OD260 | 0.38 | 0.74 | 1.95 | |
| Volume (ml) | 1 | 0.45 | 2.22 | 88% |
| B. Plasmid DNA (7.2 kb) | | | | |
| OD260 | 0.39 | 0.81 | 2.08 | |
| Volume (ml) | 1 | 0.44 | 2.27 | 91% |
| C. PCR product (500 bp) | | | | |
| OD260 | 0.43 | 0.93 | 2.16 | |
| Volume (ml) | 1 | 0.43 | 2.33 | 93% |
| D. oligonucleotide (21 nucleotides) | | | | |
| OD260 | 0.39 | 0.87 | 2.23 | |
| Volume (ml) | 1 | 0.42 | 2.38 | 94% |

Electrophoretic analysis confirmed the data presented in Table 2, showing an increased fluorescence in samples concentrated using the superabsorbing polymer beads due to higher amounts of DNA being present in the same volume. All types of DNA are efficiently concentrated by the superabsorbing polymer.

The effect of DNA concentration on superabsorbent polymer-aided DNA concentration was also evaluated. 500 µl of DNA solution isolated from human blood, approx. 30 kb, (1 µg/ml, 4 µg/ml, and 26 µg/ml) were incubated (for 40 min) in the presence of 5 superabsorbing polymer beads (produced according to example 3). 5 µl of the remaining liquid were recovered by pipetting and DNA concentration were measured spectrophotometrically. Concentration factors were 26, 22 and 19, respectively.

Example 5

Procedure for the Depletion of Cationic Compounds by Spherical Particles of poly(acrylamide-co-acrylic acid-co-N,N'-methylenebisacrylamide)

This example demonstrates the binding and absorption capacity of an anionic superabsorbent polymer for a cationic model compound. The cationic model compound (rutheniumtrisbypyridine chloride hexahydrate, 1.75 mg/ml, 500 µl) was incubated for 20 minutes with 5 superabsorbing polymer beads (produced according to example 3). The beads were than incubated with 500 µl of acetonitrile and shaken for 30 seconds. The liquid was recovered by pipetting and the concentration (0.0172 mg/ml, depletion factor of 102) was measured spectrophotometrically.

A sample of genomic DNA (from human blood, approx. 30 kb, 134 µl/ml, 500 µl) was analogously treated. The final concentration of DNA (114 µg/ml) in the liquor was determined spectrophotometrically hence indicating recovery yield of 85%.

The capacity of the superabsorbent polymer for sorption of the cationic model compound was tested in analogous experiments with rutheniumtrisbypyridine chloride hexahydrate (0.096, 0.192, 0.385, 0.770, 1.924, 3.840, 7.680, 15.360, 30.720, 76.800 mg/ml, 500 µl) essentially as described above but the last step was modified by incubating the beads with 500 µl of water or water/acetonitrile (1:1) instead of acetonitrile. The resulting concentrations of the cationic model compound in the recovered liquid were determined spectrophotometrically and are represented in Table 3 below.

TABLE 3

| mg added per sample | % sorbed Water | % sorbed acetonitrile/water 1:1 |
|---|---|---|
| 0.048 | 99.43 | 99.43 |
| 0.096 | 99.14 | 99.43 |
| 0.192 | 99.71 | 99.71 |
| 0.385 | 99.64 | 99.57 |
| 0.962 | 99.69 | 99.80 |
| 1.920 | 99.80 | 99.66 |
| 3.840 | 99.56 | 99.33 |
| 7.680 | 98.48 | 98.42 |
| 15.360 | 97.66 | 97.22 |
| 38.400 | 93.75 | 94.23 |

More than 95% of the model compound was adsorbed in all samples with concentrations of <10 mg/ml.

Example 6

Procedure for the Concentration of Azo-Albumin by Beads of poly(acrylamide-co-acrylic acid-co-N,N'-methylenebisacrylamide)

This example illustrates the time-dependent concentration of azo-albumin by superabsorbing polymer beads. A magnetically stirred solution of azo-albumin (1 mg/ml, 10 ml) was incubated with 30 or 50 superabsorbing polymer beads (produced according to example 3). Samples were recovered at defined time-points and subjected to spectrophotometrical analysis to determine azo-albumin concentration (see Table 4 below).

TABLE 4

| | rel- conc. Factor | |
| time [min] | 3 beads | 5 beads |
|---|---|---|
| 0 | 1 | 1 |
| 5 | 1.16 | 1.19 |
| 10 | 1.23 | 1.52 |
| 15 | 1.41 | 1.91 |
| 20 | 1.57 | 2.34 |
| 25 | 1.63 | 2.81 |
| 30 | 1.81 | 3.15 |
| 40 | 2.02 | 4.24 |
| 50 | 2.23 | 6.6 |
| 60 | 2.23 | |
| 90 | 2.52 | |
| 120 | 2.61 | |

In the presence of 3 beads per ml the concentration of azo-albumin in the sample essentially remains constant after 100 minutes of incubation time. In the presence of 5 beads per ml of sample the liquid is almost completely adsorbed within 50 minutes incubation time, resulting in a highly concentrated sample of azo-albumin.

Similarly, azo-albumin (1 mg/ml, 10 ml) was incubated for 20 minutes with 400, 500, 550 and 600 mg beads of superabsorbing polymer beads (produced according to Example 3) in a concentration device. The device (see FIG. 1) contains the superabsorbing polymer beads and is locked at the lower end with a cap. Concentration of a sample is performed by the following steps: 1) addition of 10 ml sample to the inner tube, 2) incubation of the sample in the inner tube for 20 minutes, 3) removal of the lower cap and positioning of the inner tube in a centrifuge tube, 4) centrifugation of the device for 5 minutes at 3000 rpm, whereby the sample is collected in the centrifuge tube. Azo-albumin concentration was again determined spectrophotometrically and the recovery yields were calculated. Fold-concentration (and recovery yields) were 2.98 (>99%), 5.43 (>98%), 7.72 (90%) and 12.2 (82%) for samples treated with 400, 500, 550 and 600 mg beads respectively.

Example 7

Procedure for Synthesis of Poly(acrylamide-co-[3-(Methacryloylamino)propyl]dimethyl(3-sulfopropyl) ammonium hydroxide) Powder Aqueous acrylamide (10 ml, 40% w/v, purum, Fluka), aqueous [3-(Methacryloylamino)propyl]dimethyl(3-sulfopropyl)ammonium hydroxide (10 ml, 30%, Aldrich) and aqueous N,N' methylenebisacrylamide (5 ml, 2% w/v, purum, Fluka) were mixed to give a precursor solution. The polymerization is initiated using ammonium peroxodisulfate/sodium pyrosulfite (50 mg of each in 1 ml water). After 1 hour the polymer block is chopped into small pieces, washed with distilled water (5 times 1 L, for 30 minutes each time) and dried in an oven (80° C.).

Example 8

Procedure for Drying and Stabilization of Urine Using Powdered poly(acrylamide-co-[3-(Methacryloylamino) propyl]dimethyl(3-sulfopropyl)ammonium hydroxide)

Poly(acrylamid-co-[3-(Methacryloylamino)propyl]dimethyl(3-sulfopropyl)ammonium hydroxid) (1.0 g, prepared according to Example 7) was added to 50 ml of human urine. After a few minutes, the liquid is completely absorbed allowing stabilization of a target molecule of interest. Without wishing to be bound by theory, it is believed that through drying the sample, small molecular weight components are absorbed and potentially protected from proteases, nucleases and other degradative enzymes, whereas high molecular weight components are not absorbed but remain protected because outside of the polymer, there is no liquid phase left thus inhibiting any degradative processes.

Example 9

Procedure for Drying and Stabilization of Blood Using Powdered poly(acrylamide-co-[3-(Methacryloylamino)propyl]dimethyl(3-sulfopropyl)ammonium hydroxide)

Poly(acrylamid-co-[3-(Methacryloylamino)propyl]dimethyl(3-sulfopropyl)ammonium hydroxide) powder prepared according to Example 7 is added to a sample of human blood sufficient to absorb the liquid phase. After a few minutes, the liquid is completely absorbed allowing stabilization of a target molecule of interest, such as RNA. This application is of particular interest in the doctor's clinic to stabilize patient samples until they reach the laboratory for analysis. As is apparent to one of ordinary skill in the art, the polymer can alternatively be provided in other forms for this purpose, for example and without limitation, in bead form using the syringe/syringe pump format of Example 1, in which a few beads of poly(acrylamid-co-[3-(Methacryloylamino)propyl] dimethyl(3-sulfopropyl)ammonium hydroxide) or other suitable superabsorbant polymer is added to the body fluid sample, e.g., blood, plasma or serum sample.

Example 10

Procedure for Synthesis of Spherical Particles of poly(acrylamide-co-3-(methacryloylamino)propyl trimethylammonium chloride-co-N,N'-methylenebisacrylamide)

Aqueous sodium alginate (12 ml; 4% w/v, low viscosity, Sigma), water (5 ml), aqueous acrylamide (4 ml, 40% w/v, purum, Fluka), aqueous [3-(Methacryloylamino)propyl] trimethylammonium chloride (4 ml, 50%, Aldrich), aqueous N,N'-methylenebisacrylamide (2 ml, 2% w/v) and N,N,N',N'-tetramethylethylendiamine (0.1 ml in 1 ml water) were mixed to give a precursor solution. The precursor solution was then filled into a syringe (syringe needle diam. of 1.2 mm) and using a syringe pump dripped (10 ml per min.) into a beaker filled with a stirred solution of ammonium peroxodisulfate (60° C., 80 ml, 1% w/v, containing 0.1 M calcium chloride) upon which spherical beads were formed. The beads are treated essentially as described above in Example 1. This process can be easily adapted to provide coated articles of manufacture, using for example the procedure of Example 2 but using acrylamide, [3-(Methacryloylamino)propyl] trimethylammonium chloride, N,N'-methylenebisacrylamide and N,N,N',N'-tetramethylethylendiamine.

Example 11

Procedure for the Depletion of Anionic Compounds by Spherical Particles of poly(acrylamide-co-3-(methacryloylamino) propyl trimethylammonium chloride-co-N,N'-methylenebisacrylamide)

An anionic model compound (Poinceaux red, 1.0 mg/ml, 500 µl) was incubated (20 minutes, 2 ml tube) in the presence of a superabsorbent polymer (produced according to Example 10: 64% w/w acrylamide, 34% w/w methacryloylamino)propyl trimethylammonium chloride and 2% w/w N,N'-methylenebisacrylamide). The beads were then incubated with 500 ml of acetonitrile and shaken for 30 seconds. The liquid was recovered by pipetting and the poinceaux red concentration (0.0075 mg/ml) was determined spectrophotometrically which corresponds to a depletion factor of 114.

An analogous experiment was performed with a nucleic acid monomer (adenosine triphosphate sodium salt, 1.0 mg/ml, 500 µl) whereby a depletion factor of 155 was reached.

A sample of genomic DNA (from human blood, approx. 30 kb, 134 µg/ml, 500 µl) was treated analogously and DNA was measured spectrophotometrically (107 µg/ml) which corresponds to a recovery yield of 80%.

Example 12

Procedure for Synthesis of Spherical Particles of poly(acrylamide-co-acrylic acid-co-N,N'-methylenebisacrylamide) and Polystyrol nanoparticles This example illustrates the preparation of a superabsorbant composite material. Aqueous sodium alginate (12 ml; 4% w/v, low viscosity, Sigma), a suspension of polystyrol nanoparticles (7 ml, 15% m/v polystyrol nanoparticles), aqueous acrylamide (8 ml, 40% w/v, purum, Fluka), aqueous N,N,N',N'-tetramethylethylendiamine (0.1 ml in 1 ml water) were mixed to give a precursor solution. The precursor solution was then filled into a syringe (syringe needle diam. of 1.2 mm) and using a syringe pump dripped (10 ml per min.) into a beaker filled with a stirred solution of ammonium peroxodisulfate (60° C., 80 ml, 1% w/v, containing 0.1 M calcium chloride) upon which spherical beads were formed. The beads are treated with alkali essentially as described above in Example 3 to provide a composite polymer with superabsorbant properties.

All publications and patent applications mentioned in this specification are herein incorporated by reference to the same extent as if each individual publication or patent application was specifically and individually indicated to be incorporated by reference. The invention now being fully described, it will be apparent to one of ordinary skill in the art that many changes and modifications can be made thereto without departing from the spirit or scope of the appended claims.

We claim:

1. A method of concentrating and purifying a nucleic acid in a liquid sample, said method comprising contacting said liquid sample having a volume and comprising said nucleic acid and a solvent with a superabsorbent polymer or a superabsorptive composite material to absorb at least a portion of the sample by said polymer or composite material, which comprises one or more polymerized anionic monomers, wherein, upon said contacting, the solvent is more efficiently sorbed than the nucleic acid and the sample is concentrated, and wherein said superabsorbing polymer or superabsorptive composite material is a powder or is comprised in a bead.

2. The method according to claim 1 where the nucleic acid is dissolved in the sample.

3. The method according to claim 2 where the sample contains additional dissolved compounds other than the nucleic acid.

4. The method according to claim 1, further comprising absorbing the further dissolved compounds in said sample with the superabsorbent polymer or the superabsorbing composite material.

5. The method according to claim 1, wherein the solvent is a hydrophilic solvent.

6. The method of claim 5, wherein the hydrophilic solvent is water or a mixture of water and a water miscible solvent.

7. The method according to claim 1, further comprising separating the nucleic acid from the superabsorbing polymers or superabsorbing composite materials, wherein said superabsorbing polymers or superabsorbing composite materials are swollen.

8. The method according to claim 1, 3, 4 or 7, wherein the superabsorbing polymer or superabsorbing composite material comprises polymerized vinylic monomers and cationic and/or zwitterionic monomers.

9. The method of claim 8, wherein said vinylic monomers are acrylic monomers, acrylic acid or methacrylic acid derivatives, or mixtures thereof.

10. The method of claim 9, wherein said acrylic acid and/or methacrylic acid derivatives are amides and/or esters thereof.

11. The method of claim 9, wherein said polymer or composite material comprises polymerized acrylate, 3-(methacryloylamino) propyl trimethylammonium chloride and/or [3-(methacryloylamino)propyl]dimethyl (3-sulfopropyl) ammonium hydroxide.

12. The method of claim 8, wherein said polymer or composite material is crosslinked.

13. The method of claim 12, wherein the said polymer is crosslinked with a crosslinking degree of 0.0001-10%.

14. The method of claim 12, wherein the said polymer is crosslinked with a crosslinking degree of 0.01-1%.

15. The method of claim 8, wherein said polymer or composite material further comprises a sorbent dispersed in said polymer.

16. The method of claim 1, wherein the nucleic acid is single-stranded or double-stranded DNA or RNA, or a combination thereof.

17. The method of claim 16, wherein the single-stranded or double-stranded DNA or RNA, or a combination thereof is genomic, viral or plasmid DNA, cDNAs, PCR products or viral RNA.

18. The method of claim 1, wherein said polymer or composite material is a co-polymer comprising polymerized ionized or ionizable acrylic monomers.

19. The method of claim 18, wherein said ionized or ionizable acrylic monomers are present in concentrations of 0.1-100% of the total monomers.

20. The method of claim 18, wherein said acrylic acid and/or methacrylic acid derivatives are amides and/or esters thereof.

21. The method of claim 1, wherein said polymer or composite material undergoes swelling upon contact with water or an aqueous solution.

22. The method of claim 1, wherein said superabsorbing polymer or superabsorbing composite material is a powder.

23. The method of claim 1, wherein said superabsorbing polymer or superabsorbing composite material is comprised in a bead.

24. The method of claim 23, wherein the bead has a diameter in range of 0.001-10 mm.

25. The method of claim 23, wherein the bead has a diameter in the range of 0.1-4 mm.

26. The method according to claim 1, wherein the superabsorbing polymer or superabsorbing composite material is comprised in a container selected from the group consisting of a sample tube, a centrifuge tube, a pipette tip, a column, a syringe and a microtiter plate.

27. The method according to claim 1, wherein said superabsorbing polymer or superabsorbing composite material is filled into, bound to, or polymerized onto said container.

28. A method of concentrating and purifying a nucleic acid in
a liquid sample
comprising
contacting said liquid sample having a volume and comprising said nucleic acid and a solvent with a superabsorbent polymer or a superabsorptive composite material to absorb at least a portion of the sample by said polymer or composite material, wherein said polymer or composite material comprising one or more polymerized anionic monomers sorbs water or hydrophilic liquids as well as low molecular weight material and wherein, upon said contacting, the solvent is more efficiently sorbed than the nucleic acid and the sample is concentrated, and wherein said superabsorbing polymer or superabsorptive composite material is a powder or is comprised in a bead.

* * * * *